United States Patent [19]

Raal

[11] Patent Number: 5,147,612

[45] Date of Patent: Sep. 15, 1992

[54] APPARATUS FOR PREPARATION OF STANDARD GAS MIXTURES

[76] Inventor: Johan D. Raal, 12 St Georges Dr., Westville, Natal, South Africa

[21] Appl. No.: 594,550

[22] Filed: Oct. 9, 1990

[30] Foreign Application Priority Data

Oct. 9, 1989 [ZA] South Africa ................. 89/7655

[51] Int. Cl.$^5$ .................. B01L 3/00; B01L 11/00; G05D 11/00
[52] U.S. Cl. .................... 422/99; 422/103; 137/88
[58] Field of Search ............... 422/99, 103, 111, 112, 422/225, 306; 137/88; 92/179, 181 P; 73/864.62

[56] References Cited

U.S. PATENT DOCUMENTS

| 3,158,072 | 11/1964 | Détrez | 92/168 |
| 4,172,670 | 10/1979 | Welker | 366/332 |
| 4,257,439 | 3/1981 | Mayeux | 137/88 |
| 4,509,409 | 4/1985 | Reeves | 92/80 |

FOREIGN PATENT DOCUMENTS 2040715A 9/1980 United Kingdom ............... 422/103

OTHER PUBLICATIONS

British Standard Methods for Preparation of Calibration Gas Mixtures, BS 4559, Part 3, 1983, ISO 6144-1981.
Blend Your Own Gas Standards Product Brochure, Astro International Corporation.

Primary Examiner—Robert J. Warden
Assistant Examiner—Christopher Y. Kim
Attorney, Agent, or Firm—Michael, Best & Friedrich

[57] ABSTRACT

Apparatus for preparation of calibration gas mixtures comprises an accurate cylinder divided into first and second chambers for two gases to be mixed in exact proportions by a piston which can be displaced by a precise linear distance by a stepper motor driven micrometer; the piston has a valved passage to allow transfer of a thus precisely determined volume from the second chamber to gas in the first chamber at balanced pressures; stirrers, temperature and pressure sensors are provided, a device for introducing vaporized drops to the gas in the first chamber is provided. The apparatus can provide mixtures in the parts per million and parts per billion ranges and one or more apparatuses can be linked to a personal computer.

8 Claims, 5 Drawing Sheets

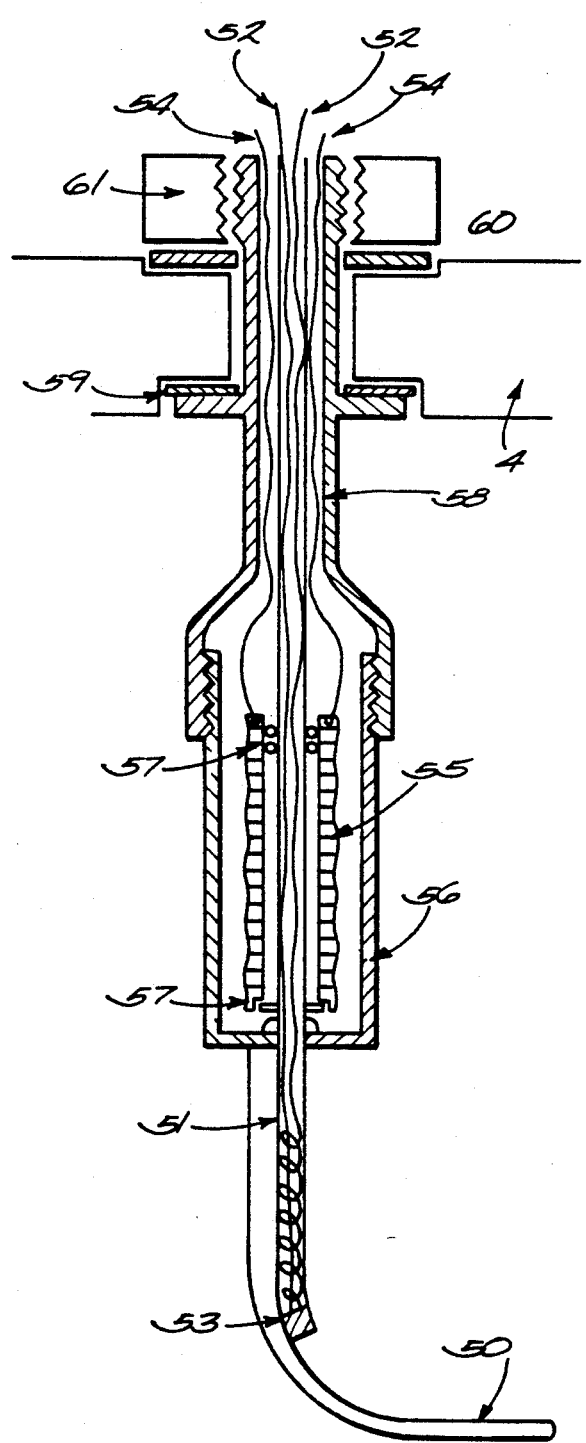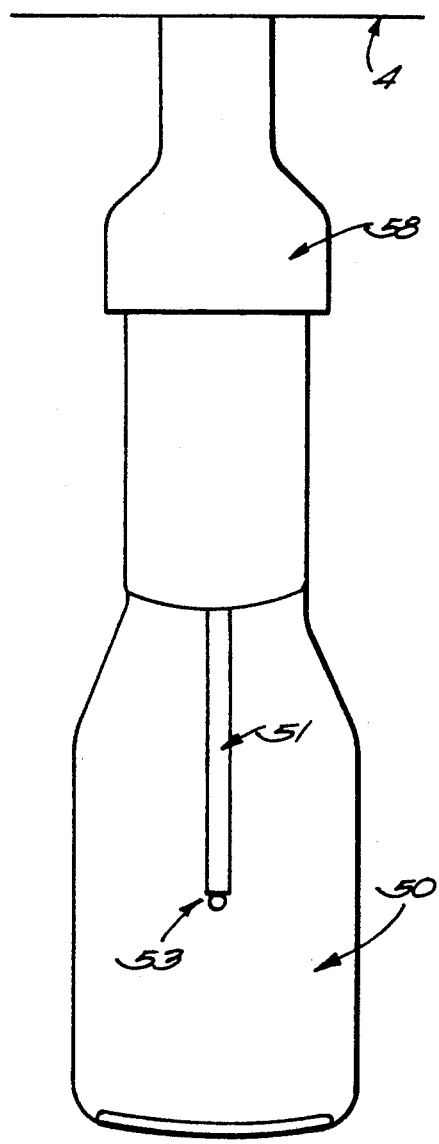

APPARATUS FOR PREPARATION OF STANDARD GAS MIXTURES

BACKGROUND OF THE INVENTION

1. Field of the Invention

The present invention relates to an apparatus for use in the preparation of gas and gas-vapor mixtures of accurately known composition, more particularly gas and gas-vapors mixtures of known composition for use in the calibration of gas chromatographs (GCs).

GCs are extensively used for the analysis of a variety of samples, the components of which may include gases, vapours and liquids. Frequently the analytes of interest in the sample are present in low, or even trace, concentrations. Since the raw data of gas chromatography are mostly obtained in the form of relative, rather than absolute, values GCs almost invariably require calibration with standard samples.

Calibration of GCs for liquid mixtures may be done by any one of several well known and satisfactory procedures.

Gas mixtures of accurately known (or at least specified) composition are readily available commercially for certain gas mixtures, but are expensive and seldom available as mixtures containing one or more uncommon components. In some cases, standard gas mixtures are known to deteriorate (i.e. change composition) with age. It would therefore be useful to have available an accurate and reliable apparatus and/or method with which to check the composition of commercially available standard gas mixtures.

2. Description of Related Art

Several devices and procedures have been described in the literature for the preparation of standard gas mixtures for use in calibrating GCs. These include gravimetric and volumetric methods, flow dilution systems, and methods utilising continuous vaporization into a gas stream, diffusion of a vapour through a capillary tube, and the use of a permeation tube. Some of these procedures and their attendant problems are reviewed in R. L. Grob (ed.) "Modern Practice of Gas Chromatography" (2nd Ed.) Wiley, 1985, and by Cowper and DeRose, "The Analysis of Gases by Chromatography", Pargamon, 1983. Most of the procedures described are subject to potential sources of error, in some cases serious sources of error, in particular because provision is seldom made for measurement of the temperature of the gases before mixing to determine, with a high degree of accuracy, the mass or the number of moles of each gas being mixed.

The most convenient and accurate method available for those wishing to prepare their own standards is the gravimetric method, i.e. by weighing. For accurate results the containers should be weighed in a vacuum, to eliminate buoyancy effects. This requirement presents severe practical difficulties in a most cumbersome procedure, particularly if a series of mixtures of different analyte concentrations is to be prepared, and effectively rules out this approach for all but the most sophisticated laboratories. Even in these laboratories, problems are encountered if the analyte is to be present in very low concentrations, e.g. in the parts per million range.

Of particular interest and relevance to the present invention are volumetric methods, such as described by the British Standards Institution BS 4559: Part 3: 1983 and in ISO standard 6144—1981: Part 3, "Static volumetric methods". Again, in the methods described in this document, no provision is made for temperature measurement of the gases or ensuring a uniform temperature before mixing. Also, reference to this document shows that the preparation of a series of standard gas mixtures of varying composition by any one of the two methods described is very cumbersome. Preparation of gas-vapour mixtures in which the vapour derives from a volatilisable liquid is given very little attention. For example, no provision is made for means to readily volatilise one or more liquid components to be introduced as the analyte(s) of interest.

A device called the Astro Digital Static Gas Blender marketed by Astro Int. Corp. of Texas and patented under U.S. Pat. No. 4,257,439 is known to applicant but is based on a sixty year old method by Burnett for studying PVT properties which is not relevant to the present invention.

BRIEF SUMMARY OF THE INVENTION

The present invention overcomes the problems associated with the prior art device and methods, by providing a compact and robust apparatus using a novel approach of linear measurement of volume. This apparatus is capable of being used readily to prepare gas mixtures of accurately known composition, for example, in several desired composition ratios, to permit calibration and the testing of a GC and its detector for linearity of response. With a small additional effort, multi-component mixtures of accurately known composition may also be prepared. Also provided is a droplet evaporator which permits the preparation of gas-vapour mixtures of which the vapour component is a liquid at ambient temperature.

The apparatus in accordance with the invention comprises in essence a two-chamber cell, one chamber (conveniently the upper chamber) of which is charged with the major, i.e. diluting (or carrier, gas component. The gas is well stirred and its temperature accurately measured with a sensor washed by the flow produced by the stirring. The second gas is contained in the lower chamber, separated from the upper chamber by a movable, gas-tight piston, and is also stirred and its temperature measured. Both gases are preferably at atmospheric pressure. By movement of the piston a precise volume of the second gas is introduced from the lower into the upper chamber by a controlled displacement of the piston, adapted to be effected without affecting the pressure in either chamber. This is achieved, as will become apparent in the description below, by maintaining a constant total interior volume of the two chambers during the mixing procedure by the incorporation of a volume change compensating mechanism.

The volume change compensation (or avoidance) mechanism proposed in preferred embodiments of the invention comprises piston rods of the same diameter on both sides of the piston arranged in such a way that upon movement of the piston the exit of a particular volume of the piston rod on one side from the cylinder, as determined by the extent of movement, is exactly balanced by the introduction of the same volume of the piston rod on the other side of the piston to the volume of the chamber on that side. In this way the total volume of the two chambers together remains the same.

A simple arrangement to achieve this would be one in which piston rods of the same diameter extend from both sides of the piston and out through both end walls of the cylinder. One thus being located in the one chamber and the other rod in the other chamber. In an alternative arrangement in one chamber the piston rod may be fixed in relation to the cylinder but penetrate a hollow space adapted to receive it in the piston to a greater or lesser degree according to movement of the piston.

Stirrers for the gases (and/or vapors) in both of the chambers can, for example, be driven by magnetic inductive forces so that no glands penetrating the cylinder walls need to be sealed against leakage.

Conveniently one piston rod which is fixed to the piston and penetrates one end wall of the cylinder is connected to a displacement means, which may be mechanical or electronic. Examples of displacement means are a vernier scale or an electronic displacement measuring means. By these, displacement of the piston can be accurately monitored and controlled. The vapourising means for supplying vapor to the interior of one chamber of the cylinder can be provided in the form of a liquid droplet dispenser arranged to dispense droplets of the liquid onto a heated spoon, by which the liquid is vapourised into the chamber.

BRIEF DESCRIPTION OF THE DRAWINGS

The equipment can operate vertically or horizontally. The invention will now be more fully described by way of examples, shown in the accompanying drawings, in which:

FIG. 2 is a schematic axial cross section of a droplet vaporizer (shown on a larger scale) for the apparatus in FIG. 1, FIG. 3 is a front view of the vaporizer in FIG. 1.

DESCRIPTION OF THE PREFERRED EMBODIMENTS

Figure 1:
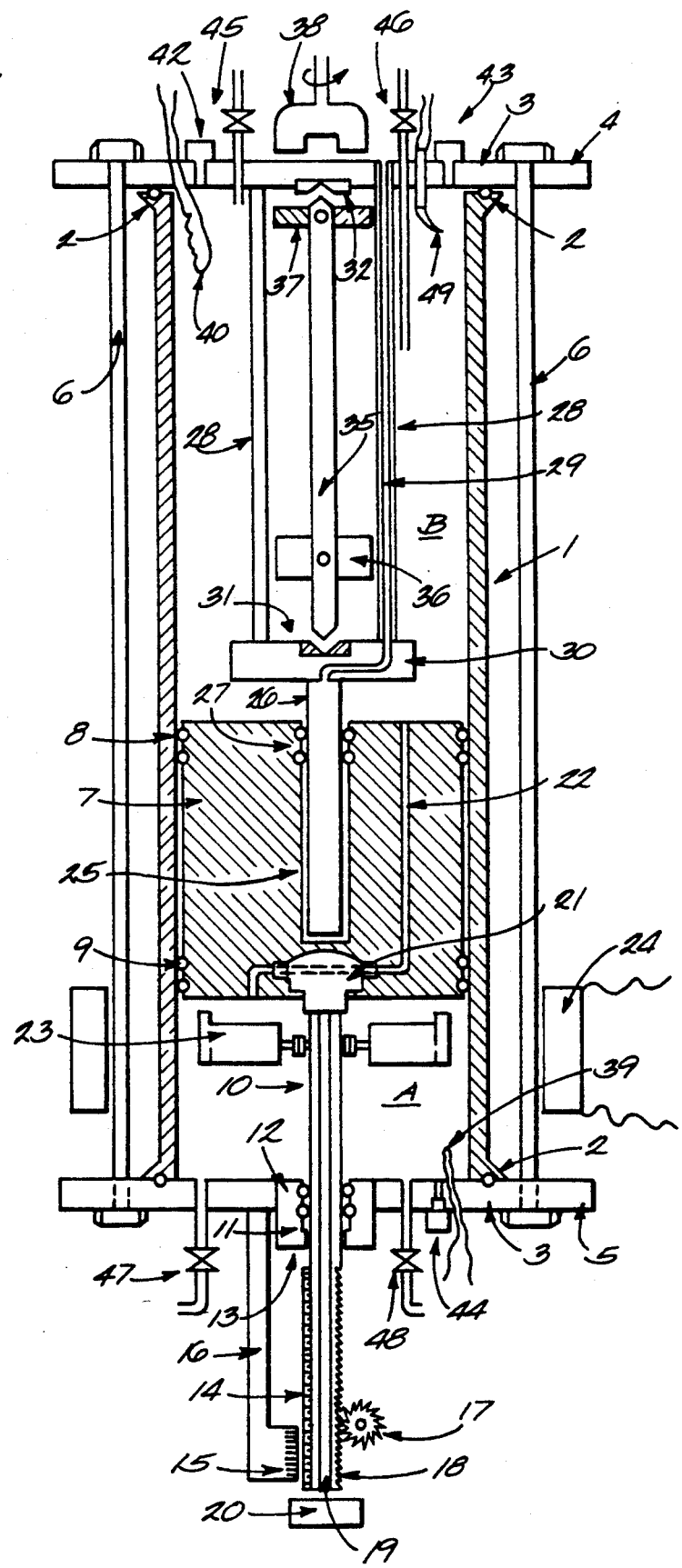
FIG. 1 is a schematic axial cross section of an apparatus, in accordance with a first preferred embodiment.

The apparatus shown in FIG. 1 comprises a heavy walled glass column 1 with a precision determined inner diameter and end sealing O-ring grooves 2 at its opposite ends in which O-rings 3 are seated to seal with stainless steel end plates 4 and 5 which are clamped onto the O-ring by means of longitudinally extending bolts 6 distributed around the circumference. A teflon piston 7 is reciprocable within the cylinder 1 and has double O-rings 8 and 9 to provide a reliable seal. The piston 7 has a piston rod 10 fixed to it which penetrates the end plate 5 through a gland 11 which has double O-rings 12 to provide a seal and a bearing surface 13. The piston 10 has a scale 14 on the portion projecting outside the cylinder which co-acts with a vernier scale 15 located on an arm 16 fixed to the end plate 5 to give an accurate measurement of the axial position of the piston. A ratchet 17 co-acts with a rack 18 for winding the piston up and down. The piston rod 10 is hollow and in its longitudinal axial bore the pin 19 of a handle 20 extends to a miniature stainless steel valve moulded into a teflon block 21 and mounted in the piston 7. This valve controls the passage of gas through a capillary gas path 22 in the piston from a lower chamber A to an upper chamber B defined by the piston in the cylinder 1. A rotating impeller 23 has embedded magnets so that a rotating-field coil 24 can cause this impeller to rotate and so mix the gas vapours in the chamber A. The opposite face of the piston to that which has the piston rod 10 fixed to it has a hollow 25 which receives a tube 26 which has the same outer diameter as that of the piston rod 10, double O-rings 27 providing a seal. The tube 26 is mounted by means of rods 28, one of which contains a passage 29 to vent to outer atmosphere air within the tube 25 as the piston 7 reciprocates. The rods 28 also carry a block 30 in which is mounted a graphitar bearing 31 which together with a graphitar bearing 32 located in the end plate 4 rotatably carries a hollow stainless steel tube 35 on which an impeller 36 is mounted. A magnet 37 affixed to the tube 35 just inside the end plate 4 is rotated by a rotating magnet 38 outside the end plate 4 to cause the impeller 36 to rotate and provide stirring of the gas and vapors in the chamber B. The temperature in the chambers A and B are measured by thermocouple detectors 39 and 40., respectively. Sample septum holders 42, 43 and 44 are provided in the end plates, as are valved connection tubes 45, 46, 47 and 48. A heated spoon 49 is provided just inside the end plate 4 onto which droplets can be dropped from the septum holder 43 to vaporize the liquid and produce a vapor as required.

Figure 1A:
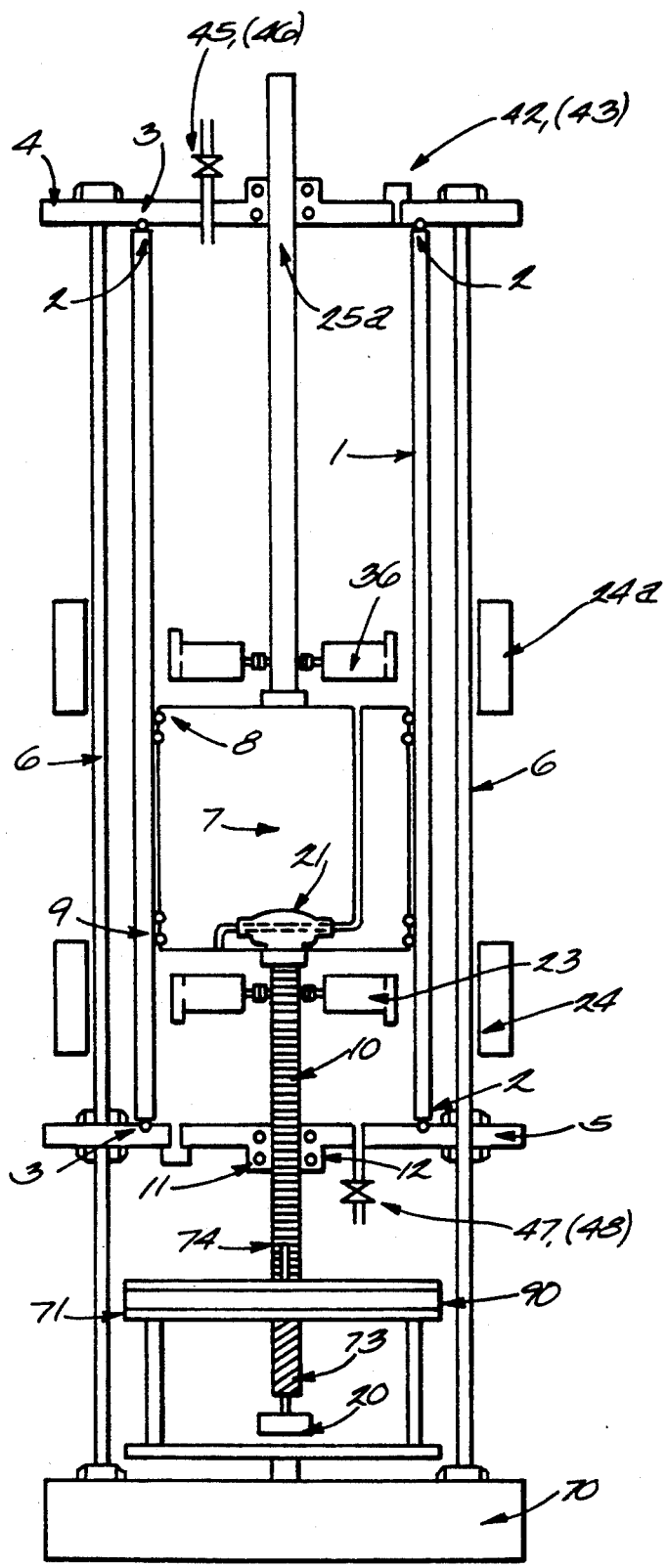
FIG. 1a shows an alternative arrangement of some components of the apparatus shown in FIG. 1.
Figure 4:
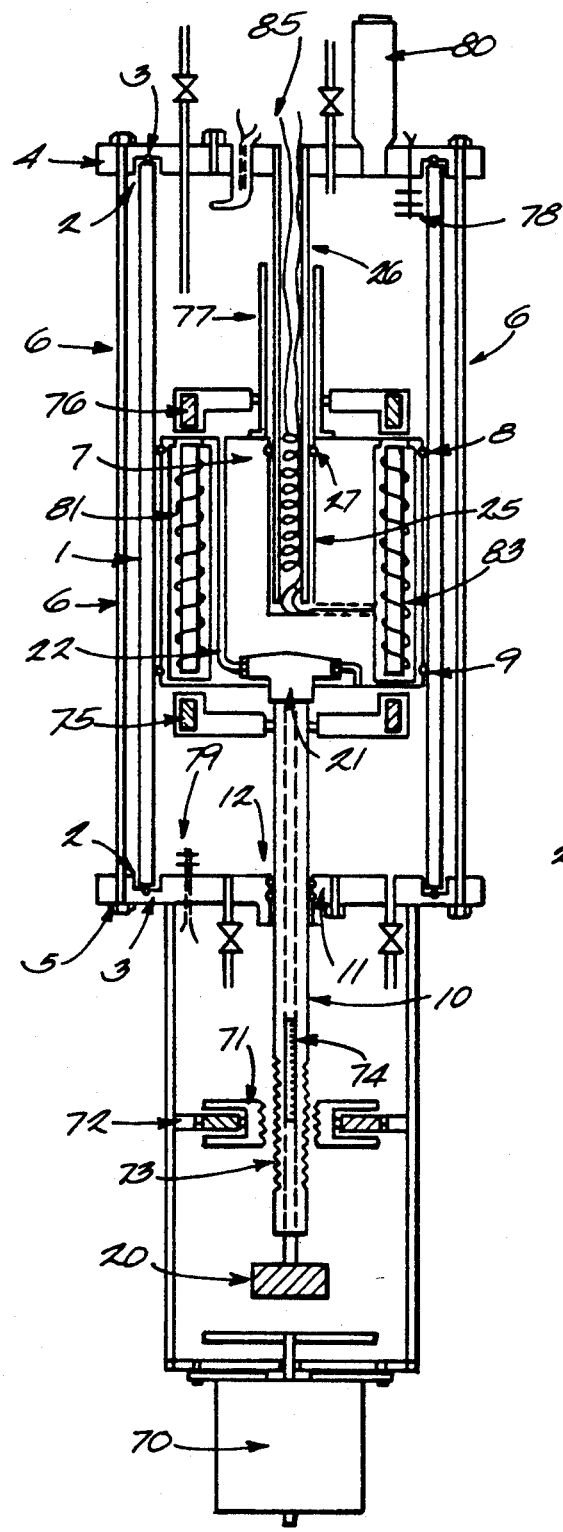
FIG. 4 is a schematic axial cross section of an apparatus in accordance with another preferred embodiment of the invention, FIG. 4a shown a possible alternative arrangement.
Figure 4A:
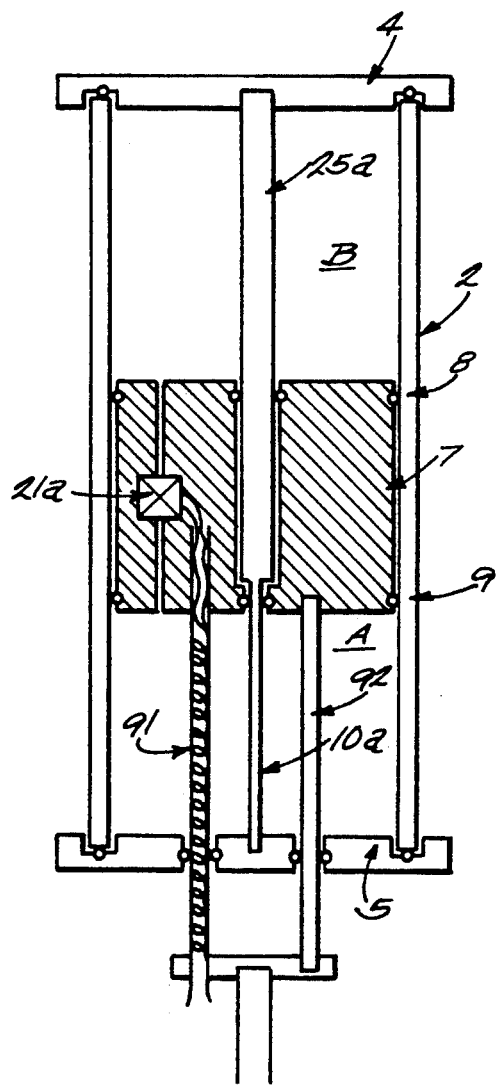

FIG. 1a shows an apparatus very similar to that of FIG. 1 save that also the first piston rod 25a is fixed to the piston 7 and penetrates the end wall 4, as does the piston rod 10. Also a stepper motor drive as shown in the embodiment of FIG. 4 is shown. The top stirrer 36a is driven much as is the bottom stirrer 23. The same reference numerals are used for analogous parts in FIGS. 1 and 4 and the descriptions with reference thereto are referred to. A micrometer scale 90 is shown.

The principle of the design is to contain a known volume of the first gas in the upper chamber B which is well stirred while or prior to its temperature being accurately measured by the sensor washed by the flow. Its pressure will be atmospheric, although higher pressures could be used if a flush mounted pressure transducer is fitted. The second gas is located in the lower chamber A of the device, separated from the upper chamber by the teflon piston with gas-tight O-ring seals. This second volume is also at atmospheric pressure, is stirred and its temperature accurately measured. A precise amount of the second gas in the lower half is propelled into the upper chamber by downward movement of the piston. This requires that the miniature stainless steel valve embedded in the piston be open just prior to the down movement of the piston. Gas in the lower chamber must perforce enter the upper chamber through the valve and capillary paths shown. The valve is then closed using the external handle on the extended shaft shown and the gas mixture formed in the upper chamber thoroughly mixed. The gas mixture at a uniform temperature can now be introduced in a GC using either a gas-tight syringe or by replacing the sample septum with a GC gas sampling device. For the latter procedure the pressure in the upper chamber could be increased slightly by moving the piston upward a small amount. It is important that pressures not be altered during the mixing procedure. To ensure this, the total interior volume of the apparatus is kept constant by virtue of the presence of tube 26 and piston rod 10 producing exactly matching increases and decreases respectively of the volumes of the two chambers as the piston moves.

The pressure rise on mixing non-ideal gases, initially at the same pressure (e.g. atmospheric) in a given volume, can be estimated accurately if the second virial coefficients in the virial equation of state are known. Extensive compilations of such data for pure gases and mixtures are available (e.g. Dymond and Smith, "The virial coefficients of pure gases and mixtures", Claredon Press (1980). The change in pressure in the upper chamber (which can be positive or negative) would affect the amount of the second gas injected into the upper chamber purely by displacement. The fractional change in pressure $$\frac{\Delta p}{p}$$

can be related to the virial coefficients and the mole fractions of the two gases in the upper chamber after complete mixing, e.g.

$$\frac{\Delta p}{p} = \frac{y_1 y_2 \sigma_{12}}{\frac{RT}{p} + y_1 B_1 + y_2 B_2} \quad (1)$$

in which
$y_1, y_2$ = mole fractions of components 1 and 2, respectively
$B_1, B_2$ = 2nd virial coefficients of pure compnents
R = gas constant
$\sigma_{12} = 2B_{12} - B_1 - B_2$ and
$B_{12}$ = virial cross coefficient for mixture.
The above expression was derived assuming the gases obey the truncated virial equation of state:

$$Z = \frac{pV}{RT} = 1 + \frac{Bp}{RT} \quad (2)$$

Calculations for several gas pairs showed that the fractional pressure change, e.g. to prepare a 30 mole % mixture of component 2, varied from as little as 0,005% [$CO_2$-ethylene] to 0,75% [$CS_2$-acetone] and 1,25% [methane-n-hexane]. The pressure change, however, would only reach the above values after complete mixing of the gases. In the proposed design, downward movement of the piston would be slow and, with the stirrers inactive, only a small amount of mixing would take place before stopping the piston movement and closure of the valve. It is believed that error from a pressure imbalance arising in the two chambers during mixing would therefore be negligible. This could, however, be monitored with a flush-fitting pressure transducer installed in the top end plate.

A more important correction is to calculate, for non-ideal gases, the number of moles of pure gas contained in the upper chamber and the number of moles of the second gas corresponding to a given volume expelled. Even at atmospheric pressure the deviation from ideal gas behaviour may amount to ~4% in some cases.

The corrections for non-ideal gases can easily be made with satisfactory accuracy if the 2nd virial coefficients are available for the gases in question. A calculation procedure could be supplied with the instrument. So for higher accuracy, exact calculations of corrections to the ideal gas law using a suitable equation of state may be made.

As an alternative to the vernier scale which can be calibrated for reading the volume change resulting from movement of the piston, a more sophisticated but more expensive procedure would be to have a moving soft iron core inside a coil to generate an analogue position indicator signal. Such transformer type coils as are used in analytical balances could be adapted and are capable of considerable accuracy. The stirring mechanisms shown are, of course, exemplary, and some alternatives could be adopted as would be apparent to those considering the drawing.

In a more expensive version the cogged wheel has been replaced by a miniature fractional kilowatt electric motor or in particular an electrical stepping motor. Since in the preferred embodiment at all times interior pressures are at or very close to atmospheric, absolute gas tightness of all the seals can be achieved reasonably easily. Slow piston movement can be adopted to avoid any possible heating of the gases by friction at the seals, and for substantial gas composition changes any temperature change by the Joule-Thompson effect can be kept very small by slow piston movement. To prevent any back flow from the upper into the lower chamber, a simple glass bead non-return valve (not shown) could be incorporated.

The septum 43 and heated spoon 49 permit the introduction of a precisely known volume of liquid at known temperature with the syringe and its complete vaporizations into a known gas volume while stirring the cell contents. This would serve as a useful calibration procedure for liquid gas mixtures in which the amount of mixed gas injected into the GC would be of constant size but varying concentrations. A thermo-couple (not shown) could be installed to check and control the vaporizer temperature, and the liquid component could act as an external standard.

It is believed that a quite compact unit embodying the apparatus in accordance with the invention could be produced. It is only necessary that the interior volume of the upper chamber be much greater than the very small amounts of stagnant gas in the two or three capillary spaces in this chamber, which would not become fully mixed with the second (introduced) gas. The capillary path in the teflon piston leading to the upper chamber may be shortened considerably from that shown with only fairly minor re-design. The volume of the lower chamber would dictate the range of possible gas compositions. It is probably desirable to aim only for mixtures up to 50; larger concentrations would require reversal of the two gases. The diameter vs length ratio of the cell should not directly influence the accuracy of measurement, and the diameter would be dictated largely by the difficulty of incorporating the various fittings in the upper chamber end plate. With appropriate miniaturisation it should be possible to restrain interior diameter to about 50 to 60 mm. For the preparation of compositions in the parts per million range (e.g. for atmospheric pollutants) it would be desirable to redesign the unit with a lower chamber of much smaller diameter. No new principles would be involved, but the upper chamber stirrer would require a substantial re-design, for vapor-gas mixtures in the ppm range the upper chamber and droplet evaporator only need to be used. For accuracy of addition, a dilute solution of the desired material in a pure, volatile solvent could be added from a syringe.

A dedicated micro-computer could be attached to monitor piston travel temperature and pressure and to incorporate calculation for nonideality of the gases.

To restrain temperature changes owing to heat exchange with the surroundings, it may be necessary to surround the unit with a perspex air chamber and to introduce thermal breaks in the lower exterior metal extensions, or to house the unit in a constant temperature air bath. This has not been found necessary in inventor's experience.

Accurate temperature measurement is vital to determine the total number of moles of gas contained in a given volume. Temperatures must also be uniform and constant for a reasonable length of time in each chamber prior to mixing. Sufficiently accurate temperature measurements can be obtained with thermocouples or Pt 100 sensors if these are carefully installed. In particular the installations must have small thermal capacity (for rapid response), must be well insulated from the stainless steel end plates, and must have minimum conductive paths along the leads.

The liquid droplet vaporizer shown in FIGS. 2 and 3 comprises a stainless steel evaporating surface 50 of spoon-like shape on which a stainless steel tube 51 conducts the wires 52 for a thermocouple 53. Wires 54 are connected to a ceramic cartridge heater 55 contained in a stainless steel tube 56, and asbestos gaskets 57 hold the cartridge heater in relation to the tube 51. The body 58 of the device is mounted in the container wall 4 with sealing gaskets 59 and insulating gaskets 60, held down by a nut 61.

Referring to FIG. 4 the same reference numerals are used for components which correspond to components with those references in FIG. 1 and the following description will be substantially confined to the points of difference.

The ratchet mechanism 17, 18 shown in FIG. 1 has been discarded in favor of movement by a stepper motor 70. The motor 70 rotates a brass nut 71 held in a ball bearing 72 in such a way that the rotating nut cannot move upwards or downwards. Its rotation around the threaded shaft 73 propels the shaft upwards or downwards depending on the direction of rotation of the reversible stepper motor. Rotation of the shaft is prevented by a guide pin moving in a vertical slot in the shaft (not shown).

Linear movement of the piston shaft is measured on the micrometer arrangement built into the propelling mechanism. The small linear millimeter scale 74 is fixed into a shallow recess on the piston shaft which does not interfere with the rotation of the brass nut around the shaft. The top of the rotating brass nut has a plate provided radially into 20 marked divisions and thus forms a micrometer scale that divides each millimeter of thread into 20 divisions (more divisions can be used for finer discrimination if needed).

An even finer measurement of linear travel is to count the number of steps taken by the stepper motor which, with 1.80 per step thus divides ones rotation (i.e. 1 mm of thread spacing) into 200 divisions, i.e. 0.005 mm vertical travel per motor step.

The stirrers 75 and 76 in the bottom and top compartments respectively are again rotated by rotating magnetic fields. The top stirrer is fixed onto the shaft 77 which is fixed onto the piston 7. The piston is made of teflon (other materials, e.g. stainless steal, can be used) and has steel end plates. The bottom stirrer is fixed onto the outer shaft leading from the valve 21. Stirrer 76 has hollow passages adapted to serve as a centrifugal impeller with valve 77 as an intake; strong stirring can be achieved with an adequate electrical drive. Both stirrers are driven by rotating magnetic fields generated by fixed coils mounted around the outside of the glass cylinder 6. The magnetic fields in these external coils (not shown) are rotated by an electronic module.

Gas temperatures in the top and bottom compartments are measured with PT-100 (Platinum resistance bulb) sensors embedded in thin walled stainless steel tubes, 78 and 79, protruding into the two respective compartments. The containing tubes were thermally isolated from the steel end plates in which they are mounted and are provided with thin circular fins to increase the surface area for heat transfer and thus to enhance the rate at which the sensor temperatures approach the gas temperatures.

A precise pressure transducer 80 is mounted in the top steel end plate 4 and displays very accurately the pressure in the top compartment.

In the preferred embodiment, FIG. 4, the external magnetic coils have been replaced by means of a construction in which magnetic coils are embedded in the teflon piston itself, for example four vertical magnetic coils. All surfaces were sealed gas-tight and the electrical leads were brought out through the hollow rod protruding through the wall in the upper surface of the piston. This also brought the stationary and rotating magnetic poles close together for a more powerful stirring. Vertical coils 81 and 83 are shown in FIG. 4 together with the windings and the electrical leads 85 which are coiled to allow extensive compression as the piston moves up and down.

The cross sectional area of piston rod 25a is equal to the sum of the cross sectional areas of the piston rod 10a and rods 90 and 91. Rod 91 is hollow tocoonvey wires to control the valve 21a. The apparatus shown in FIG. 4 was used for a series of tests as follows:

TEST 1: Pressure (P)—-Volume (V)—-Temperature (T) studies

Pure propane was placed in the top compartment by displacing all air in the compartment. With the communicating valve in the piston closed the stirrer was rotated until temperature equilibrium was established. The temperature and pressure of the gas and the position of the piston (i.e. micrometer reading) were noted. With the communicating valve remaining closed the piston was moved down a few centimeters. Temperature equilibrium was again established and T, P and micrometer readings were again noted. The procedure was repeated for a further expansion of the propane.

If there are no leakages in any part of the system the P—V—T reading should obey an equation of state such as the ideal gas law or a more precise equation such as the Virial equation of state, $$Z = \frac{pV}{RT} = 1 + \frac{Bp}{RT}$$

(R=ideal gas constant, V=specific volume, T=absolute temperature, p=absolute pressure, B=second Virial coefficient=a function of temperature only).

The readings can also be used as a convenient method of finding the initial volume of the top compartment before the gas expansion.

It can easily be shown that the change in Volume $\Delta V$ between two piston positions is related to the temperature and pressure readings by:

$$n = \text{No of moles of gas} = \frac{\Delta V}{\frac{RT_2}{P_2} - \frac{RT_0}{P_0} + R(B_2 - B_0)}$$

The volume change is related to the piston movement $\Delta L$ by:

$$\Delta V = \frac{\pi}{4}(D_O{}^2 - d_i{}^2)\Delta L$$

Where
($D_O$ = inside diameter of glass cylinder = 76.26 mm
($d_i$ = outside diameter of stainless steel rod attached to piston = 13.85 mm

| Piston position (mm) | Pressure (kPa) | Temperature (K) | Calculated value of n, gm moles |
|---|---|---|---|
| 0 | 102,3 | 292 | — |
| 10,8 | 77,95 | 292 | 0,006410 |
| 13,3 | 73,90 | 293 | 0,006414 |

As seen from the last column, the No. of gm-moles of gas, n, remains exactly constant as it should. This indicates accurate gas Volume, temperature and pressure measurement and the absence of any leaks.

TEST 2: MIXING EXPERIMENT

Procedure

Mixture of Carbon Dioxide ($CO_2$) in Propane ($C_3H_8$) were prepared by filling the top compartment with $C_3H_8$ and the bottom compartment with $CO_2$. After thermal equilibrium ($\pm 15$ minutes) pressures in the top and bottom compartments were equalized by venting each chamber, where the pressure was slightly above atmospheric, to the atmosphere ($\pm 5$ seconds).

The communicating valve was then opened and the piston moved downwards a distance. The valve was closed and the stirrers activated to produce complete mixing and thermal equilibrium. Temperature, pressure and piston position readings were then taken. This procedure was repeated a few times. After each mixing procedure, a sample of the gas was analyzed on a gas chromatograph (G.C.).

Results

The mole fraction of a gas (1) in a binary mixture is related to the areas obtained on a G.C. integrator by:

$$x_1 = \text{mole fraction of (1)} = \frac{A_1 F_1}{A_1 F_1 + A_2 F_2}$$

$F_1$, $F_2$ = response factors for components (1) and (2)
Rearrangement of this equation gives:

$$\frac{A_1}{A_2} = \left(\frac{F_2}{F_1}\right)\left(\frac{x_1}{1 - x_1}\right)$$

Figure 5:
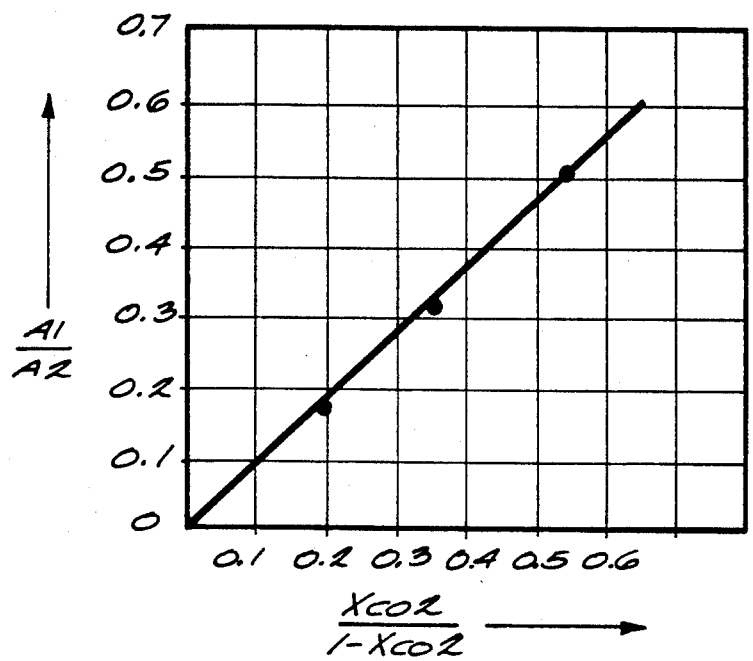
FIGS. 5 and 6 are graphical representation of test results.
Figure 6:
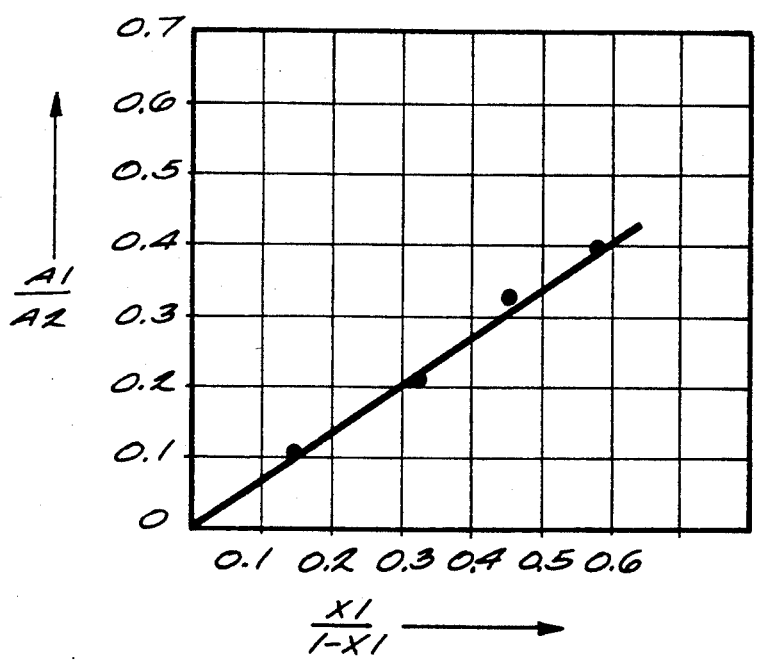

Thus, for a "linear response" i.e., if the ratio of response factors $F_1/F_2$ = constant, a plot of area ratios $A_1/A_2$ vs the mole fraction ratio $(x_1/1-x_1)$ should be a straight line through the origin. The slope of this line is the desired ratio of response factors, $F_1/F_2$, required for calibration of the G.C. FIGS. 5 and 6 show plots obtained in this way for two separate series of experiments using two different gas chromatographs. The linearity of response of the G.C. detectors is fully confirmed and illustrated by these results.

Instead of a precision glass cylinder a stainless steel cylinder could be used. This would simplify construction but it would not be possible to see the operation of the stirrers or the operation of the droplet vaporizer (e.g. partial recondensation of vaporized liquid on the colder glass surfaces would not be visible. Alternatively a stainless steel cylinder might be used with glass and plates or with glass windows in the end plates. This would represent some problem in construction but many of the fittings now mounted on the stainless steel end plates could then be mounted in the upper and lower cylinder walls. Operation of the equipment in the gas mixing mode could be simplified by mounting a differential pressure transducer in the piston. Small movements of the piston could then be used to produce exactly equal pressures, not necessarily atmospheric pressure, in the two compartments, i.e. the two compartments would not have to be vented to atmosphere to equalise pressures before opening the communicating valve. This would mean a more expensive version. Possibly a differential pressure transducer could be developed that simultaneously gives the absolute pressure in both compartments, this would be mounted inside the piston communicating with both compartments. This is considered unnecessary since in all mixing experiments the pressure inside the vessel remained absolutely constant during piston movement.

It may be possible to incorporate the instrument into a gas chromatograph cabinet and to use the existing electronics available. Further economy in regard to the electronics and software can be achieved by the provision of a single electronics package to run more than one instrument.

Thus the priciple of the instrument of the present invention is based on a linear measurement of volume. This can be done to very high levels of accuracy depending on the accuracy of machining of the cylinder and the calibration of the drive of the piston and reference has been made above for example to calibration to 0.005 mm. Since the instrument operates at atmospheric pressure most gases are nearly ideal in their properties and correction for non-ideality is small and easily made.

The equation for calculating gas mole fraction can be arranged as follows:

$$x_A = \frac{1}{1 + \frac{\Delta L}{L'}\left[\frac{Z_A T_A}{Z_B T_B}\right]}$$

where
L = measured linear distance of piston travel
L = effective initial volume before addition of second gas (known accurately)
$Z_A, Z_B$ = compressibility factors for gases A and B at temperatures $T_A$ and $T_B$, usually the same, and at the same (atmospheric) pressure.

For pure gases the factors $Z_A$ and $Z_B$ are given conveniently by the Virial equation of state, $$\text{e.g. } Z_A = 1 + \frac{B_A p}{RT}$$

At low pressure the 2nd term is usually of the order 0.01 or less and B is known for most gases to an accuracy of +2%. Any error introduced in the composition calculation due to pure gas non-ideality is then very small indeed, of the order of 0.04%. The principle of operation is thus very sound and the potential accuracy 0.04% is far beyond that achievable by certain prior art instruments.

Indeed for small concentrations, particularly, the accuracy competes with that of the most accurate method known, the gravimetric method with weighing in a vacuum to compensate for buoyancy.

Although not specifically designed for trace amounts it is believed the device is unmatched in the extremely dilute ranges for accuracy and ease of operation.

A single step of the stepper motor, for example (1.80) will inject a volume of the second gas equal to 1 part in 20,000 into the pure gas in the upper chamber, i.e. 50 parts per million. Smaller concentrations can easily be achieved by closer spacing of the threads on the piston rod. Also, another dilution, e.g. by displacing the diluted gas from the top compartment into pure gas in the bottom compartment will give increments (per step of the stepper motor) of 0.0025 parts per million, i.e. 2.5 parts per billion. Moreover, the accuracy is self-testing in that plots of $A_1/A_2$ vs mole fraction ratio $x_1/x_2$ must be linear and must plot through the origin for all concentrations. No other device that I am aware of other than analysis by mass spectrometer, can compete with my invention in this very dilute (or any other) concentration range.

The instrument can moreover be implemented in a design which has very good portability and is sturdy, compact and light. The electronic module is a separate unit and easily can be replaced remotely from the mixing unit. Thus a single electronic module can operate many stainless steel mixing units placed next to operating gas chromatographs giving a very cost effective method indeed since the mixing unit itself is fairly inexpensive. Moreover, the electronic module could be interfaced with available personal computers using an appropriate software package.

The instrument is also well adapted for measuring pressure, volume and temperature relationship of gas mixtures. This information is often lacking but of vital importance to the chemical process industries.

Suitable embodiments can moreover be adapted to serve as a primary calibration standard. It can readily be connected to the sampling manifold and operated automatically if the valve handle operating the communicating valve between the cell halves is replaced by an electrically operated rotary valve as used in gas chromatographic equipment.

I claim:

1. An apparatus for use to prepare gas mixtures of accurately known composition which comprises a cylinder having a first end wall at one end and a second end wall at the other end, a piston movable in the cylinder and sealing with the cylinder walls, said piston and cylinder defining a first chamber on a first side of the piston and a second chamber on a second side of the piston, means defining a hole in the first side of said piston, a first piston rod fixed to the first end wall and slidable into said hole in the first side of the piston and sealing with the hole defining means, means defining a hole in the second end wall, a second piston rod connected to the second side of the piston and exiting from the second chamber through the hole in the second end wall and sealing with the hole defining means therein, a device for causing linear movement and for measuring that movement, said device being couple to and acting on the second piston rod outside the cylinder, the first and second piston rods having the same diameter, a valved passage penetrating the piston from the first side to the second side, stirring means mounted on the piston rod located in at least one of the chambers, valve means for admission of gas to each chamber and valve means for extracting gas from each chamber.

2. An apparatus as claimed in claim 1 and including a liquid drop vaporizer which has an attached electrical heating means, located inside the first chamber, shaped to hold liquid dropped onto the liquid drop vaporizer.

3. An apparatus as claimed in claim 1 and including a temperature measurement means so located inside the first chamber that the gas circulated by the mixing means flows over the temperature measurement means.

4. An apparatus as claimed in claim 1 and including stirring means in both chambers, driving means outside the cylinder and magnetically coupled to the stirring means for rotatably driving the stirring means through the cylinder walls without any structural connection between the driving and stirring means.

5. An apparatus as claimed in claim 1, in which the linear movement and measurement device comprises a nut outside the cylinder threaded on a thread on the second piston rod which exists from the cylinder, the nut rotatively fixed in axial position relative to the piston rod, a stepper motor for rotating the nut and a micrometer scale positioned for indicating linear movement of the piston.

6. An apparatus for use to prepare gas mixtures of accurately known composition which comprises a cylinder having a first end wall at one end and a second end wall at the other end, a piston having first and second sides and movable in the cylinder and sealing with the cylinder walls, said piston and cylinder defining a first chamber on the first side of the piston and a second chamber on the second side of the piston, means defining first and second holes in the first and second end walls, respectively, a first piston rod fixed to the first side of the piston and exiting from the first chamber through the first hole in the first end wall and sealing with the hole defining means therein, a second piston rod connected to the second side of the piston and exiting from the second chamber through the second hole in the second end wall and sealing with the hole defining means therein, a device for causing linear movement and for measuring that movement, said device acting on the second piston rod outside the cylinder, the first and second piston rods having the same diameter, a passage penetrating the piston from the first side to the second side and having a valve therein, the valve in the passage being openable and closable by means of a rod which passes through a bore in the second piston rod to outside of the apparatus, stirring means mounted on the piston rod and located in at least one of the chambers, valve means for admission of gas to each chamber and valve means for extracting gas from each chamber.

7. An apparatus for use in preparing gas mixtures of accurately known composition, said apparatus comprising a cylinder, a piston having first and second sides and movable within said cylinder and sealing therewith for defining a first chamber on the first side of the piston and a second chamber on a second side thereof, a first piston rod fixed to the first side of the piston and extending in a sealed relation through the wall of said cylinder and a second piston rod connected to the second side of the piston and extending in a sealed relation through the wall of said cylinder, means coupled to one of said piston rods for moving said piston and means for measuring said movement, a passage formed in said piston for communicating the first and second sides thereof and first valve means disposed within said passage, valve operating means for opening and closing said first valve means, stirring means disposed within at least one of said chambers and second valve means for admitting and extracting gas from each chamber.

8. An apparatus for use in preparing gas mixtures of accurately known composition, said apparatus comprising a cylinder, a piston having first and second sides and movable within said cylinder and sealing therewith for defining a first chamber on the first side of the piston and a second chamber on a second side thereof, a first piston rod fixed to the first side of the piston and extending in a sealed relation through the wall of said cylinder and a second piston rod connected to said cylinder and extending in a sealed relation through the second side of said piston, means coupled to one of said piston rods for moving said piston and means for measuring said movement, a passage formed in said piston for communicating the first and second sides thereof and first valve means disposed within said passage, valve operating means for opening and closing said first valve means, stirring means disposed within at least one of said chambers and second valve means for admitting and extracting gas from each chamber.

* * * * *